US012773175B2

(12) United States Patent
Yan et al.

(10) Patent No.: US 12,773,175 B2
(45) Date of Patent: Oct. 27, 2026

(54) METHOD FOR GENERATION OF A MULTI-MODALITY IMAGE SET AND ELECTRONIC DEVICE

(71) Applicant: OUR UNITED CORPORATION, Shaanxi (CN)

(72) Inventors: Hao Yan, Shaanxi (CN); Haifeng Liu, Shaanxi (CN)

(73) Assignee: OUR UNITED CORPORATION, Shaanxi (CN)

( * ) Notice: Subject to any disclaimer, the term of this patent is extended or adjusted under 35 U.S.C. 154(b) by 0 days.

(21) Appl. No.: 18/931,444

(22) Filed: Oct. 30, 2024

(65) Prior Publication Data

US 2025/0134484 A1 May 1, 2025

(30) Foreign Application Priority Data

Oct. 31, 2023 (CN) ......................... 202311437911.6

(51) Int. Cl.

| | |
|---|---|
| ***A61B 6/00*** | (2024.01) |
| ***G01R 33/48*** | (2006.01) |
| ***G01R 33/56*** | (2006.01) |
| ***G06T 7/00*** | (2017.01) |
| ***G06T 12/10*** | (2026.01) |
| ***G06T 12/30*** | (2026.01) |

(52) U.S. Cl.

CPC ............ *A61B 6/5247* (2013.01); *A61B 6/481* (2013.01); *G01R 33/5608* (2013.01); *G06T 7/0016* (2013.01); *G06T 12/10* (2026.01); *G06T 12/30* (2026.01); *G01R 33/481* (2013.01); *G06T 2207/10084* (2013.01); *G06T 2207/30096* (2013.01); *G06T 2210/41* (2013.01); *G06T 2211/444* (2023.08); *G06T 2211/464* (2023.08)

(58) Field of Classification Search

CPC .. A61B 6/481; A61B 6/5247; G01R 33/5608; G01R 33/481; G06T 11/005; G06T 11/008; G06T 7/0012; G06T 7/0016

See application file for complete search history.

(56) References Cited

U.S. PATENT DOCUMENTS

| | | | | |
|---|---|---|---|---|
| 2012/0002857 A1* | 1/2012 | Song | ...................... | A61B 6/032 382/131 |
| 2014/0235995 A1* | 8/2014 | Owen | .................. | G01R 33/286 600/411 |
| 2023/0334664 A1* | 10/2023 | Lu | ............................ | G06T 7/20 |
| 2024/0122556 A1* | 4/2024 | Hiasa | ................... | A61B 6/5235 |
| 2024/0335174 A1* | 10/2024 | Slomka | .................. | A61B 6/481 |

OTHER PUBLICATIONS

Wang, Jihong, et al. "Magnetic resonance imaging of glucose uptake and metabolism in patients with head and neck cancer." Scientific reports 6.1 (2016): 30618.*

* cited by examiner

*Primary Examiner* — Carolyn A Pehlke
(74) *Attorney, Agent, or Firm* — The Webb Law Firm

(57) ABSTRACT

A method for generating the multi-modality image set, including obtaining a first modality image of an target for radiotherapy, where the first modality image is an image generated from the target for radiotherapy, and the target for radiotherapy is injected with a tracer; and performing a modality conversion on the first modality image to obtain the multi-modality image set of the target for radiotherapy.

16 Claims, 3 Drawing Sheets

METHOD FOR GENERATION OF A MULTI-MODALITY IMAGE SET AND ELECTRONIC DEVICE

CROSS-REFERENCE TO RELATED APPLICATION

This application claims priority to Chinese Patent Application No. 202311437911.6, filed Oct. 31, 2023, the disclosure of which is hereby incorporated by reference in its entirety.

BACKGROUND OF THE INVENTION

Field of the Invention

The present disclosure relates to the field of medical technology, and in particular, to a method for generating a multi-modality image set and an electronic apparatus.

Description of Related Art

In a radiotherapy diagnosis phase in the field of medical technology, in general, multiple scans need to be performed on a target for radiotherapy (e.g., a patient) according to different sites of the target for radiotherapy and imaging requirements, so as to obtain images of different modalities such as a magnetic resonance imaging (MRI) image, a computed tomography (CT) image, a cone-beam computed tomography (CBCT) image, and then the images of different modalities are used to perform radiotherapy diagnosis.

SUMMARY OF THE INVENTION

In an aspect, a method for generating a multi-modality image set is provided, and includes: obtaining a first modality image of a target for radiotherapy, where the first modality image is an image generated from the target for radiotherapy, and the target for radiotherapy is injected with a tracer; and performing a modality conversion on the first modality image to obtain the multi-modality image set of the target for radiotherapy.

In another aspect, an electronic apparatus is provided, and includes: at least one processor, and a memory communicatively connected to the at least one processor.

The memory stores instructions executable by the at least one processor, and the instructions are executed by the at least one processor, so as to enable the at least one processor to be configured to: obtain a first modality image of a target for radiotherapy, where the first modality image is an image generated from the target for radiotherapy, and the target for radiotherapy is injected with a tracer; and perform a modality conversion on the first modality image to obtain the multi-modality image set of the target for radiotherapy.

In yet another aspect, a non-transitory computer-readable storage medium is provided. The non-transitory computer-readable storage medium stores computer program instructions that, when executed by a processor, cause the processor to implement the method for generating the multi-modality image set according to the present disclosure.

In yet another aspect, a computer program product is provided. The computer program product includes a computer program that, when executed by a processor, cause the processor to implement the method for generating the multi-modality image set according to the present disclosure.

It should be understood that what is described in the summary is not intended to identify critical or significant features of the embodiments of the disclosure, nor is it intended to limit the scope of the present disclosure. Other features of the present disclosure will become readily understood from the following description.

BRIEF DESCRIPTION OF THE DRAWINGS

The accompanying drawings are used to understand the present solution and do not constitute a limitation of the present disclosure.

DESCRIPTION OF THE INVENTION

Figure 1:
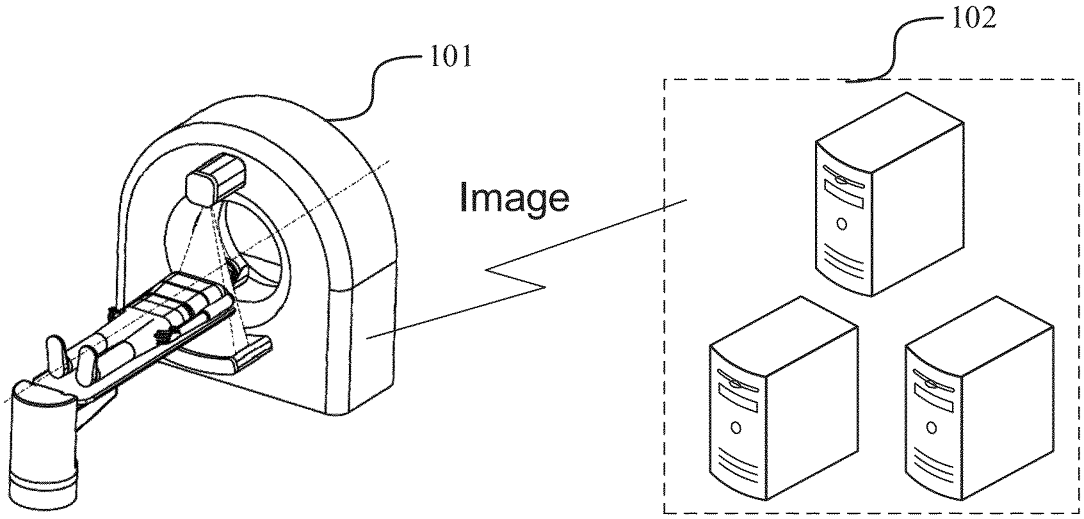
FIG. 1 is a schematic diagram of an implementation environment of a method for generating a multi-modality image set, in accordance with some embodiments of the present disclosure.

Some embodiments of the present disclosure will be clearly and completely described below with reference to the accompanying drawings. However, the described embodiments are merely some but not all embodiments of the present disclosure. All other embodiments obtained by a person of ordinary skill in the art based on embodiments of the present disclosure shall be included in the protection scope of the present disclosure.

Unless the context requires otherwise, throughout the specification and the claims, the term "comprise" and other forms thereof such as the third-person singular form "comprises" and the present participle form "comprising" are construed as an open and inclusive meaning, i.e., "including, but not limited to."

In the description of the specification, the terms such as "some embodiments", "example" or "some examples" are intended to indicate that specific features, structures, materials or characteristics related to the embodiment(s) or example(s) are included in at least one embodiment or example of the present disclosure. Schematic representation of the above terms do not necessarily refer to the same embodiment(s) or example(s). In addition, the specific features, structures, materials or characteristics may be included in any one or more embodiments or examples in any suitable manner.

Hereinafter, the terms "first" and "second" are used for descriptive purposes only, and are not to be construed as indicating or implying the relative importance or implicitly indicating the number of indicated technical features. Thus, features defined with "first" or "second" may explicitly or implicitly include one or more of the features. In the description of the embodiments of the present disclosure, the term "a plurality of" or "the plurality of" means two or more unless otherwise specified.

In the description of some embodiments, the term "connected," and derivative thereof may be used. The term "connected" should be understood in a broad sense. For example, the term "connected" may represent a fixed connection, a detachable connection, or a one-piece connection, or may represent a direct connection, or may represent an indirect connection through an intermediate medium.

The phrase "at least one of A, B and C" has a same meaning as the phrase "at least one of A, B or C", and they both include the following combinations of A, B and C: only A, only B, only C, a combination of A and B, a combination of A and C, a combination of B and C, and a combination of A, B and C.

As used herein, the term "if" is optionally construed as "when" or "in a case where" or "in response to determining" or "in response to detecting", depending on the context. Similarly, depending on the context, the phrase "if it is determined . . . " or "if [a stated condition or event] is detected" is optionally construed as "in a case where it is determined . . . ", "in response to determining . . . ", "in a case where [the stated condition or event] is detected" or "in response to detecting [the stated condition or event]".

The phrase "configured to" used herein means an open and inclusive expression, which does not exclude devices that are configured to perform additional tasks or steps.

In addition, the use of the phrase "based on" is meant to be open and inclusive, since a process, step, calculation or other action that is "based on" one or more of the stated conditions or values may, in practice, be based on additional conditions or values beyond those stated.

Exemplary embodiments of the present disclosure are described below with reference to the drawings, in which various details of some embodiments of the present disclosure are included to facilitate understanding, and these embodiments should be considered as exemplary only. Therefore, those skilled in the art should realize that various changes and modifications can be made to the embodiments described herein without departing from the scope of the present disclosure. Similarly, for clarity and conciseness, description of well-known functions and structures have been omitted from the following description.

First, application scenarios involved in some embodiments of the present disclosure are introduced. A method for generating a multi-modality image set provided by some embodiments of the present disclosure may be applied in the field of medical technology, for example, in a scenario of radiotherapy.

In a radiotherapy diagnosis phase in the field of medical technology, in general, multiple scans need to be performed on a target for radiotherapy (e.g., a patient) according to different sites of the target for radiotherapy and imaging requirements, so as to obtain images of different modalities such as an MRI image, a CT image, a CBCT image, and then the images of different modalities are used to perform the radiotherapy diagnosis. However, when performing the multiple scans on the target for radiotherapy, it may easily cause serious harm to the target for radiotherapy due to the accumulation of radiation doses.

Based on this, some embodiments of the present disclosure provide a method for generating the multi-modality image set. For example, the method is a method for generating the multi-modality image set based on digital twin.

For example, an image, generated from a target for radiotherapy, and the target for radiotherapy is injected with a tracer, is used as a first modality image, and a multi-modality image set of the target for radiotherapy is generated through a modality conversion. In this way, a plurality of images of the target for radiotherapy of different modalities may be obtained by scanning the target for radiotherapy only once instead of scanning the target for radiotherapy multiple times, thereby avoiding the serious harm to the target for radiotherapy due to the accumulation of radiation dose.

Moreover, the multi-modality image set of the target for radiotherapy is generated through the digital twin, so that a reference image of the target for radiotherapy is enriched, which may provide more reference basis for medical personnel, thereby increasing the amount of information referenced for radiotherapy and providing a guarantee for precise radiotherapy.

FIG. 1 is a schematic diagram of an implementation environment of a method for generating a multi-modality image set, in accordance with some embodiments of the present disclosure. Referring to FIG. 1, the implementation environment includes an image acquisition apparatus 101 and an image server 102.

For example, the image acquisition apparatus 101 is used to acquire images including a tumor and surrounding normal tissues of the target for radiotherapy.

For example, the image acquisition apparatus 101 may be an MRI apparatus or a PET-CT apparatus.

In some embodiments of the present disclosure, the image acquisition apparatus 101 is used to acquire the first modality image of the target for radiotherapy injected with the tracer, and send the first modality image of the target for radiotherapy to the image server 102.

For example, the first modality image may be an MRI image or a PET-CT image.

In some embodiments, the image server 102 may be an independent physical server.

In some embodiments, the image server 102 may be a server cluster or a distributed file system composed of a plurality of physical servers.

In some embodiments, the image server 102 may be at least one of basic cloud computing services such as a cloud service, a cloud database, a cloud computing, a cloud function, a cloud storage, a network service, a cloud communication, a middleware service, a domain name service, a security service, a content distribution network, and a big data or artificial intelligence platform. However, the present disclosure is not limited thereto, which are not limited in the present disclosure.

In some embodiments, the implementation environment may include more or fewer of the above-mentioned image servers 102, which is not limited in the present disclosure. Of course, the image server 102 may further include other functions to provide more comprehensive and diverse services.

In some embodiments of the present disclosure, the image server 102 is used to obtain the first modality image of the target for radiotherapy, and perform a modality conversion on the first modality image to obtain the multi-modality image set of the target for radiotherapy.

For example, in a case where the first modality image is an MRI image, the multi-modality image set may include at least one of an MRI image, a CT image, a CBCT image, a PET image, a PET-MRI image, a PET-CT image, and an optical epidermal image.

For example, in a case where the first modality image is a PET-CT image, the multi-modality image set may include at least one of a CT image, a CBCT image, a PET image, a PET-CT image, and an optical epidermal image.

In some embodiments of the present disclosure, the image server 102 further includes an image database. The image database is used to store object identifications of a plurality of targets for radiotherapy and corresponding multi-modality image sets.

In some embodiments, the image database is further used to store the object identifications of the plurality of targets for radiotherapy at different moments and the corresponding multi-modality image sets.

Hereinafter, the method according to some embodiments of the present disclosure will be introduced based on the implementation environment shown in FIG. 1.

Figure 2:
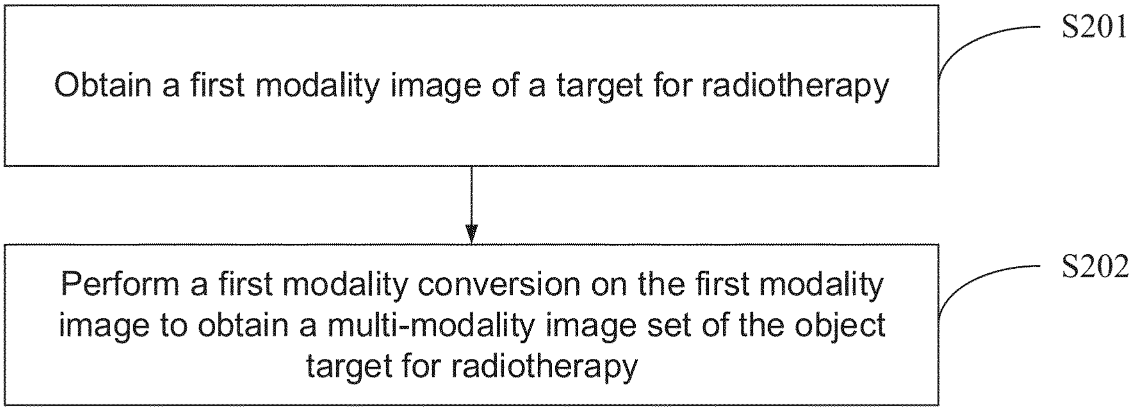
FIG. 2 is a flow diagram of a method for generating a multi-modality image set, in accordance with some embodiments of the present disclosure.

FIG. 2 is a flow diagram of a method for generating a multi-modality image set, in accordance with some embodiments of the present disclosure. In some embodiments, the method for generating the multi-modality image set is performed by an electronic apparatus. For example, the electronic apparatus may be the image server shown in FIG. 1 above. As shown in FIG. 2, the method includes the following step S201 to step S202.

In step S201, a first modality image of a target for radiotherapy is obtained.

For example, the target for radiotherapy is used to refer to as a patient to be treated with radiotherapy or a phantom simulating a patient. The first modality image is an image generated from the target for radiotherapy injected with the tracer.

For example, the tracer is used to visualize the tumor of the target for radiotherapy in an image.

In this way, the first modality image may reflect not only the tissue structure information of the target for radiotherapy, but also the biological metabolism information of the target for radiotherapy.

In some embodiments, the first modality image may be an MRI image generated by an MRI apparatus or a PET-CT image generated by a PET-CT apparatus.

In a case where the first modality image is an MRI image, the tracer may be a sugar tracer. For example, the tracer may be a form of glucose. It can be understood that the MRI image here may reflect not only the tissue structure information of the target for radiotherapy, but also the biological metabolism information of the target for radiotherapy.

For example, in a case where the first modality image is a PET-CT image, the tracer may be a PET nuclide. For example, the tracer may be a positron nuclide. It can be understood that the PET-CT image here is a fusion image of the PET image and the CT image. The PET image may reflect the biological metabolism information of the target for radiotherapy, and the CT image may reflect the tissue structure of the target for radiotherapy.

In step S202, a multi-modality image set of the target for radiotherapy is obtained by performing a modality conversion on the first modality image.

In some embodiments, in a case where the first modality image is an MRI image, the multi-modality image set includes at least one of an MRI image, a CT image, a CBCT image, a PET image, a PET-MRI image, a PET-CT image, and an optical epidermal image.

In some embodiments, in a case where the first modality image is a PET-CT image, the multi-modality image set includes at least one of a CT image, a CBCT image, a PET image, a PET-CT image, and an optical epidermal image.

Some embodiments of the present disclosure provide a method for generating the multi-modality image set based on digital twin. The method uses an image, generated from a target for radiotherapy, and the target for radiotherapy is injected with a tracer, as a first modality image, and generates a multi-modality image set of the target for radiotherapy through modality conversion.

In this way, a plurality of images of the target for radiotherapy of different modalities may be obtained by scanning the target for radiotherapy only once instead of scanning the target for radiotherapy multiple times, thereby avoiding the serious harm to the target for radiotherapy due to the accumulation of radiation dose.

Moreover, the multi-modality image set of the target for radiotherapy is generated through the digital twin, so that a reference image of the target for radiotherapy is enriched, which may provide more reference basis for medical personnel, thereby increasing the amount of information referenced for radiotherapy and providing a guarantee for precise radiotherapy.

The method for generating the multi-modality image set according to the present disclosure will be described below.

Figure 3:
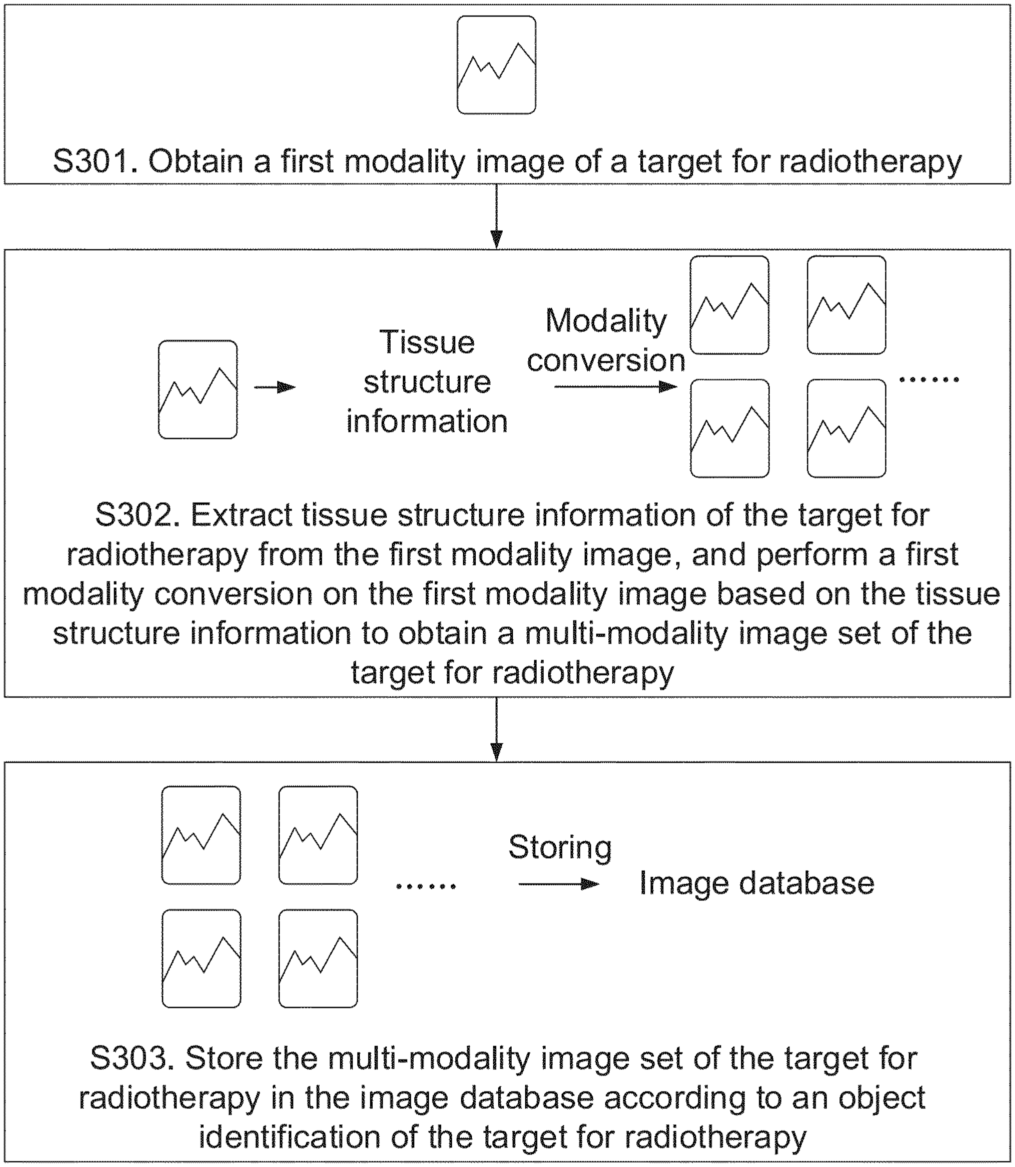
FIG. 3 is another flow diagram of a method for generating a multi-modality image set, in accordance with some embodiments of the present disclosure.

FIG. 3 is another flow diagram of a method for generating a multi-modality image set, in accordance with some embodiments of the present disclosure. In some embodiments, the method for generating the multi-modality image set is performed by an electronic apparatus. For example, the electronic apparatus may be the image server shown in FIG. 1 above. As shown in FIG. 3, with the image server as an execution body, the method includes the following steps S301 to S303.

In step S301, the image server obtains a first modality image of a target for radiotherapy.

In some embodiments of the present disclosure, the target for radiotherapy is used to refer to as a patient to be treated with radiotherapy or a phantom simulating a patient. The first modality image is an image generated from the target for radiotherapy injected with the tracer.

For example, the first modality image may be a nuclear magnetic resonance image used to reflect the biological metabolism information of the target for radiotherapy. The tracer is used to highlight the tumor in the patient to be radiotherapy for easy imaging.

In some embodiments, the first modality image may be an MRI image or a PET-CT image.

For example, in a case where the first modality image is an MRI image, the tracer may be a type of glucose that is not radioactive.

It will be noted that after glucose is injected into the target for radiotherapy, glucose may implement a high aggregation effect in the tumor due to the metabolism of glucose in the tumor of the target for radiotherapy, and thus the tumor may be presented in the image.

For example, in a case where the first modality image is a PET-CT image, the tracer may be a PET nuclide, such as a positron nuclide.

It will be noted that after injecting the PET nuclide into the target for radiotherapy, the PET nuclide is used as an imaging agent, so as to label human metabolites such as glucose. The imaging agent is then taken up by the tumor, which may also enable the PET nuclide to implement a high aggregation effect at the tumor, thereby causing the tumor to be presented in the image.

In some embodiments, for the target for radiotherapy injected with the tracer, after the first modality image of the target for radiotherapy is acquired by the image acquisition apparatus, the image acquisition apparatus sends the first modality image of the target for radiotherapy to the image server. Correspondingly, the image server receives the first modality image from the image acquisition apparatus, that is, obtains the first modality image of the target for radiotherapy.

In some embodiments, for the target for radiotherapy injected with the tracer, after the first modality image of the target for radiotherapy is acquired by the image acquisition apparatus, the first modality image of the target for radiotherapy is output.

For example, the first modality image output in this case may be in a form of a data packet file or in a form of a physical image. Furthermore, the medical personnel uploads the first modality image output by the image acquisition apparatus to the image server, and the image acquisition apparatus obtains the first modality image of the target for radiotherapy.

It is worth noting that the image server may further adopt other implementation manners to obtain the first modality image of the target for radiotherapy, which is not limited in the present disclosure.

In some embodiments, taking the first modality image as an MRI image as an example, the target for radiotherapy injected with glucose is scanned by the MRI apparatus, and the MRI image of the target for radiotherapy may be obtained by scanning.

In this way, the modality conversion based on the MRI image may be implemented by acquiring the MRI image of the target for radiotherapy as the first modality image, thereby completing the conversion of the multi-modality image set of the target for radiotherapy.

On the one hand, since there is no ionizing radiation in the MRI image, the radiation hazard to the target for radiotherapy may be fundamentally avoided. On the other hand, since the MRI image includes a rich amount of information, such as rich tissue structure information, the subsequent modality conversion using the MRI image may obtain other modality image including more information, thereby improving the generation effect of the multi-modality image set.

In some embodiments, taking the first modality image as a PET-CT image as an example, the target for radiotherapy injected with the PET nuclide is scanned by the PET-CT apparatus, and the PET-CT image of the target for radiotherapy may be obtained by scanning.

In this way, by acquiring the PET-CT image of the target for radiotherapy as the first modality image, the modality conversion based on the PET-CT image may be implemented, thereby completing the conversion of the multi-modality image set of the target for radiotherapy.

In some embodiments, the MRI image of the target for radiotherapy may be preferentially acquired as the first modality image. In a case where the target for radiotherapy does not support the acquisition of MRI image, the PET-CT image of the target for radiotherapy may be acquired as the first modality image.

For example, if metal is implanted in the body of the target for radiotherapy, it is impossible to use the MRI apparatus to acquire the MRI image. In this case, the PET-CT apparatus may be used to acquire the PET-CT image as the first modality image.

In step S302, the image server extracts tissue structure information of the target for radiotherapy from the first modality image, performs modality conversion on the first modality image based on the tissue structure information, and obtains a multi-modality image set of the target for radiotherapy.

The tissue structure information is used to characterize the tissue structure of the site to be radiotherapy of the target for radiotherapy. For example, the tissue structure of the tumor of the target for radiotherapy.

In some embodiments, in a case where the first modality image is an MRI image, the multi-modality image set includes at least one of an MRI image, a CT image, a CBCT image, a PET image, a PET-MRI image, a PET-CT image, and an optical epidermal image.

In some embodiments, in a case where the first modality image is a PET-CT image, the multi-modality image set includes at least one of a CT image, a CBCT image, a PET image, a PET-CT image, and an optical epidermal image.

In this way, by utilizing the tissue structure determined in the first modality image, the multi-modality image set of the target for radiotherapy may be generated through the digital twin, so that the plurality of images of different modalities may be obtained without scanning the target for radiotherapy multiple times, thereby avoiding the serious harm to the target for radiotherapy due to accumulation of radiation dose. Moreover, the multi-modality image set of the target for radiotherapy is generated through the digital twin, so that the reference images of the target for radiotherapy are enriched, and the amount of reference information for radiotherapy may be increased. Compared with radiotherapy relying on single-modality image data in related art, the solutions according to some embodiments of the present disclosure improve the accuracy of radiotherapy and may provide the guarantee for precise radiotherapy.

In some embodiments, the process of performing a modality conversion based on the organizational structure information may refer to any one of the two possible implementation methods shown in (1-1) and (1-2) below.

In the implementation method (1-1), the image server extracts an image block including the tissue structure from the first modality image based on an image extraction algorithm, so as to obtain the tissue structure information. The image server inputs the tissue structure information into a first modality conversion model, processes the tissue structure information through the first modality conversion model, and obtains the multi-modality image set of the target for radiotherapy.

For example, the image extraction algorithm is used to extract an image block including a target image feature, such as the image block including the tissue structure. For example, the image extraction algorithm may be an image feature extraction algorithm based on a histogram of oriented gradient (HOG), or an image feature extraction algorithm based on deep learning.

After the tissue structure information is extracted based on the image extraction algorithm, the first modality conversion model is used to perform the modality conversion, so as to obtain the multi-modality image set of the target for radiotherapy. For example, the first modality conversion model may provide the tissue structure information based on an original modality image, thereby implementing the function of modality conversion.

In some embodiments, the first modality conversion model may be obtained by training an initial model based on first training data.

For example, the first training data may include tissue structure information of a plurality of first modality sample images and corresponding multi-modality sample images.

It will be noted that the initial model may be iteratively trained by using the first training data before implementing the solution, so as to obtain the above-mentioned first modality conversion model. And then, the first modality conversion model may be maintained in the image server, so that the first modality conversion model may be used for the modality conversion subsequently.

Accordingly, the above-mentioned iterative training process may include that during any iterative training process, the tissue structure information of the first modality sample image is input into the model obtained after a previous iterative training, so as to obtain an image output result of this iterative training, and a model parameter is adjusted based on the image output result and the multi-modality sample image corresponding to the first modality sample image, and performing a next iterative training based on the adjusted model parameter.

The above process of adjusting the model parameter includes that a model loss value of this iterative training is determined based on the image output result and the multi-modality sample image, and the model parameter is adjusted according to the model loss value. The model loss value is used to represent a difference between the image output result of the model and the multi-modality sample image. In some embodiments, the model loss value may be a cross entropy loss value or a mean square error loss value (MSE).

In this way, since the model loss value is used to represent the difference between the image output result of the model and the multi-modality sample image, the learning ability of the model may be improved by determining the model loss value and adjusting the model parameter according to the model loss value, thereby training and obtaining a model with good learning ability.

It will be noted that the model loss value may further include other types of model loss values, so as to perform the above process of adjusting the model parameter according to the model loss value, which is not limited in the present disclosure.

In some embodiments, the above-mentioned iterative training process may further include that it is determined whether the model training has reached a target condition after adjusting the model parameter, so that a next iterative training is performed based on the adjusted model parameter in a case where the model training is not reached the target condition, and the model training is stopped until the model training reaches the target condition.

For example, the target condition satisfies at least one of the following conditions: a number of iterations of model training reaches a target number; or the model loss value is less than or equal to a target threshold.

For example, the target number is a preset number of training iterations. For example, the number of iterations reaches 100. The present disclosure does not limit the setting of the target number. The target threshold is a preset fixed threshold. For example, the model loss value is less than 0.0001. The present disclosure does not limit the setting of the target threshold.

In implementation method (1-2), the image server inputs the first modality image into a second modality conversion model, and extracts the tissue structure information in the first modality image through a feature extraction layer of the second modality conversion model. The tissue structure information is processed by a feature processing layer of the second modality conversion model, so as to obtain the multi-modality image set of the target for radiotherapy.

For example, the second modality conversion model has a function of performing a modality conversion based on the original modality image.

In some embodiments, the second modality conversion model may be obtained by training the initial model based on second training data.

For example, the second training data may include a plurality of first modality sample images and corresponding multi-modality sample images, such as a plurality of first modality sample images of different radiotherapy objects and corresponding multi-modality sample images.

It will be noted that, before implementing the solution, the initial model may be iteratively trained by using the second training data, so as to obtain the above-mentioned second modality conversion model, and the second modality conversion model may be maintained in the image server.

Correspondingly, the above-mentioned iterative training process includes that during any iterative training process, the first modality sample image is input into the model obtained after a previous iterative training, so as to obtain an image output result of this iterative training, and the model parameter is adjusted based on the image output result and the multi-modality sample image corresponding to the first modality sample image, and performing a next iterative training based on the adjusted model parameter.

It will be noted that the process of adjusting the model parameter and determining whether the target condition is satisfied in the above implementation method (1-2) may be found in the content of implementation method (1-1), which will not be repeated here.

Furthermore, in some of the above embodiments, the process of modality conversion is described by taking the first modality conversion model and the second modality conversion model as examples. In some embodiments, other implementation methods may be used to complete the modality conversion, which is not limited in the present disclosure.

In some of the above embodiments, the process of performing a modality conversion on the first modality image to obtain the multi-modality image set of the target for radiotherapy is described by taking the tissue structure information as an example.

In some embodiments, the image server may further perform the above-mentioned modality conversion process in combination with vital sign data of the target for radiotherapy at a current moment. The corresponding process may include that the image server obtains the vital sign data of the target for radiotherapy at the current moment. Based on the vital sign data of the target for radiotherapy at the current moment, the first modality image of the target for radiotherapy at a historical moment is modally converted, so as to obtain a multi-modality image set matched with the vital sign data of the target for radiotherapy at the current moment.

For example, the vital sign data may be two-dimensional vital sign data, such as body surface data (e.g., weight), or three-dimensional vital sign data, such as volume data. It will be noted that the vital sign data refers to vital sign data of the site of the target for radiotherapy other than the tumor and the new lesion area.

In some embodiments, the process of the image server acquiring the vital sign data of the target for radiotherapy at the current moment may include that a contour reconstruction processing is performed on the vital sign data of the target for radiotherapy at the historical moment, so as to obtain the vital sign data of the target for radiotherapy at the current moment.

For example, the contour reconstruction process may be a process of performing an extrapolation process on the basis of local vital sign data to obtain the complete vital sign data. For example, the complete body surface data may be obtained by performing the extrapolation processing on the basis of local body surface data, and further vital sign data of internal tissues may be obtained through the extrapolation processing.

In this way, on the basis of tissue structure information, the modality conversion is performed in combination with the vital sign data of the target for radiotherapy at the most recent moment, and the reference is made to the changes in vital signs of the target for radiotherapy in the time dimension, such as gaining weight or losing weight, thereby increasing the amount of information referenced by the modality conversion and improving the accuracy of the modality conversion.

In step S303, the image server stores the multi-modality image set of the target for radiotherapy in the image database according to the object identification of the target for radiotherapy.

The object identification is used to uniquely identify the target for radiotherapy. For example, the object identification may be an object name, an object number, or an object identity document (ID).

In some embodiments, the image server may include an image database for storing object identifications of a plurality of targets for radiotherapy and corresponding multi-modality image sets.

It will be understood that for different targets for radiotherapy, the generation solution of the multi-modality image set provided by some embodiments of the present disclosure may be utilized to generate the image data of the plurality of different modalities, and then store the image data of different modalities of different targets for radiotherapy.

In addition, the image server may further send the multi-modality image sets of different targets for radiotherapy to the cloud server for storage by the cloud server.

In this way, multi-modality image sets of targets for radiotherapy in different medical institutions may be shared. For example, data may be shared with medical personnel to achieve remote diagnosis and radiotherapy teaching, etc., thereby forming a data cloud with a virtuous ecological cycle of resource sharing.

In some embodiments, the image server converts the first modality image of the target for radiotherapy into the second modality image in response to the target for radiotherapy in the image database lacking the second modality image in the multi-modality image set, so as to obtain the second modality image of the target for radiotherapy.

For example, the second modality image may be one or more images lacking from the multi-modality image set. In this way, the image database may be monitored through the image server, so as to determine whether there are one or more lacking images, and then the modality conversion of the lacking images is completed, thereby completing the data update of the image database.

In some embodiments, the image database is further used to store the object identifications of the plurality of targets for radiotherapy at different moments and the corresponding multi-modality image sets.

In some embodiments, the image server determines timing difference information in response to a first modality image at a first moment in which the target for radiotherapy is lacking in the image database, based on at least one modality image in the multi-modality image set at the first moment and at least one modality image in the multi-modality image set at a second moment. In addition, the image server converts the first modality image at the second moment into the first modality image at the first moment based on the timing difference information, so as to obtain the first modality image of the target for radiotherapy at the first moment.

For example, the timing difference information is used to characterize the change difference of the target for radiotherapy between the first moment and the second moment.

For example, the first moment may be before the second moment. Accordingly, through the above implementation method, a first modality image at a later moment may be converted into a first modality image at a previous moment based on the timing difference information between a multi-modality image set at a previous moment and a multi-modality image set at a later moment, thereby obtaining the first modality image of the target for radiotherapy at the previous moment.

For example, the first moment may be after the second moment. Accordingly, through the above implementation method, a first modality image at a previous moment may be converted into a first modality image at a later moment based on the timing difference information between a multi-modality image set at a later moment and a multi-modality image set at a previous moment, thereby obtaining the first modality image of the target for radiotherapy at the later moment.

It will be noted that the timing difference information between two moments may be determined based on one modality image, two modality images, or a plurality of modality images in the multi-modality image sets at the two moments.

For example, taking a modality image A1 and a modality image A2 at the first moment, and a modality image B1 and a modality image B2 at the second moment as an example, a process of determining the timing difference information between the two moments may include: determining timing difference information C1 between the modality image A1 at the first moment and the modality image B1 at the second moment, determining timing difference information C2 between the modality image A2 at the first moment and the modality image B2 at the second moment, and fusing the timing difference information C1 and the timing difference information C2 to obtain timing difference information between the two moments.

For example, the fusion processing may be a weighted summation process or other processing methods, which is not limited in the present disclosure.

In some embodiments, after obtaining the multi-modality image set of the target for radiotherapy, the image server may select a target modality image that satisfies a preset condition from the multi-modality image set. The target modality image is used to perform at least one of an image registration process, an image fusion process, an image guidance process and a radiotherapy plan generation process of the target for radiotherapy.

It will be noted that the preset condition may be a preset condition for screening target modality images.

The image registration process refers to a process of matching two or more images acquired at different times, using different imaging apparatuses, or under different conditions (e.g., shooting angles or shooting positions).

The image fusion process refers to a process of fusing two or more images into one image.

The image guidance process refers to a process of using acquired images to monitor the tumor and normal tissue before and during radiotherapy, and adjusting the radiotherapy position and radiotherapy condition according to the change in organ position, so that an irradiation field of the treatment apparatus closely follows the target volume.

The radiotherapy plan generation process refers to formulating a corresponding radiotherapy plan for the patient based on the medical data of the patient before radiotherapy.

For example, the preset condition may be set to be related to the process to be executed, and accordingly, the target modality image that satisfies the preset condition is the target modality image related to the process to be executed.

In some embodiments, taking the image registration process as an example, the target modality image related to the image registration process may be a CT image at an initial moment (e.g., a CT image in an initial radiotherapy plan).

Accordingly, the CT image at the initial moment may be selected as the target modality image for rigid registration with the CBCT image acquired at a latest moment.

In some embodiments, the target modality image related to the image registration process may be an MRI image at an initial moment (e.g., an MRI image in an initial radiotherapy plan). Accordingly, the MRI image at the initial moment may be selected as the target modality image for rigid registration with the CBCT image acquired at a latest moment.

In some embodiments, the target modality image related to the image registration process may be a CT image P at an initial moment and a CT image Q corresponding to a CBCT image at a latest moment. Accordingly, the CT image P at the initial moment and the CT image Q corresponding to the CBCT image at the latest moment may be selected as target modality images to perform rigid registration between the CT image P and the CT image Q.

It will be noted that the CT image Q here may be a CT image obtained by performing a modality conversion on the CBCT image acquired at the latest moment. In this way, in the image registration process, not only the latest CBCT image in the time dimension but also the CT image or MRI image with the highest resolution in the spatial dimension are taken into account, thereby optimizing the image registration process.

In some embodiments, in the image fusion process, the target modality images related to the image fusion process may be an MRI image and a CT image. Accordingly, the MRI image and CT image may be selected for the fusion processing.

In some embodiments, the target modality images related to the image fusion process may be a PET image and a CT image. Accordingly, the PET image and the CT image may also be selected for the fusion processing.

In some embodiments, the target modality images related to the image fusion process may be a CBCT image and a CT image. Accordingly, the CBCT image and the CT image may also be selected for the fusion processing.

In some embodiments, in the image guidance process, the target modality image related to the image guidance process may be a CT image. Accordingly, the CT image may be selected for the image guidance.

In some embodiments, the target modality image related to the image fusion process may be an MRI image. Accordingly, the MRI image may also be selected for the image guidance.

In some embodiments, in the radiotherapy plan generation process, the target modality image related to the radiotherapy plan generation process may be a CT image. Accordingly, the CT image may be selected to generate the radiotherapy plan.

In some embodiments, the target modality image related to the radiotherapy plan generation process may be an MRI image. Accordingly, the MRI image may also be selected to generate the radiotherapy plan.

In some embodiments, the preset condition may also be set to an optimal radiotherapy effect. Accordingly, the target modality image that satisfies the preset condition is the target modality image with the optimal radiotherapy effect.

In some embodiments, in the image registration process, considering the high accuracy of image registration between images of the same modality, the CT image P at the initial moment and the CT image Q corresponding to the CBCT image at the latest moment may be selected as the target modality images with the optimal radiotherapy effect. Furthermore, the CT image P at the initial time and the CT image Q corresponding to the CBCT image at the latest time are used as the target modality images to perform rigid registration between the CT image P and the CT image Q.

In some embodiments, after the image registration is performed based on the CT image P and the CT image Q, the CT image Q may be used as the target modality image with the optimal radiotherapy effect in the subsequent image guidance process. For example, after the image registration is performed on the CT image P and the CT image Q, the target for radiotherapy is moved according to the registration result.

In some embodiments, taking the radiotherapy plan generation process for soft tissue as an example, considering that the resolution of the soft tissue imaging in the MRI image is high, the MRI image may be selected as the target modality image with the optimal radiotherapy effect, and then the MRI image may be used to generate the radiotherapy plan for soft tissue.

In this way, based on the advantages and disadvantages of different modality images, the target modality image with the optimal radiotherapy effect may be selected to perform processes such as radiotherapy planning, image registration, image guidance, etc., which may provide guarantees for precise radiotherapy.

It will be noted that the preset condition may further be set to other types of conditions, which is not limited in the present disclosure.

In some of the above embodiments, the tissue structure information of the first modality image of the same target for radiotherapy may be used to generate image data of different modalities through the digital twin, and further, radiotherapy diagnosis and radiotherapy may be performed on the target for radiotherapy based on the image data of different modalities.

Compared with the related art, the solutions provided by some embodiments of the present disclosure only require a single scan of the target for radiotherapy to obtain the MRI image or the PET-CT image, so as to obtain the plurality of images of the target for radiotherapy in different modalities, which may provide more reference basis for medical personnel, thereby increasing the amount of information referenced for radiotherapy and providing the guarantee for precise radiotherapy.

The technical solutions provided by some embodiments of the present disclosure provide a method for generating the multi-modality image set based on the digital twin. The method uses the image generated from the target for radiotherapy injected with the tracer as the first modality image, and generates the multi-modality image set of the target for radiotherapy through the modality conversion.

In this way, the plurality of images of the target for radiotherapy of different modalities may be obtained by scanning the target for radiotherapy only once instead of scanning the target for radiotherapy multiple times, thereby avoiding the serious harm to the target for radiotherapy due to the accumulation of radiation dose.

Moreover, the multi-modality image set of the target for radiotherapy is generated through the digital twin, so that the reference image of the target for radiotherapy is enriched, which may provide more reference basis for medical personnel, thereby increasing the amount of information referenced for radiotherapy and providing the guarantee for precise radiotherapy.

Some embodiments of the present disclosure further provide an electronic apparatus. The electronic apparatus includes at least one processor and a memory communicatively connected to the at least one processor.

The memory stores instructions executable by the at least one processor, and the instructions are executed by the at least one processor, so as to enable the at least one processor to execute the method for generating the multi-modality image set provided by some embodiments of the present disclosure.

Some embodiments of the present disclosure further provide a non-transitory computer-readable storage medium storing computer instructions. The computer instructions are used to enable the electronic apparatus to execute the method for generating the multi-modality image set provided by some embodiments of the present disclosure.

Some embodiments of the present disclosure further provide a computer program product, which includes a computer program that, when executed by a processor, implements the method for generating the multi-modality image set provided by the present disclosure.

Figure 4:
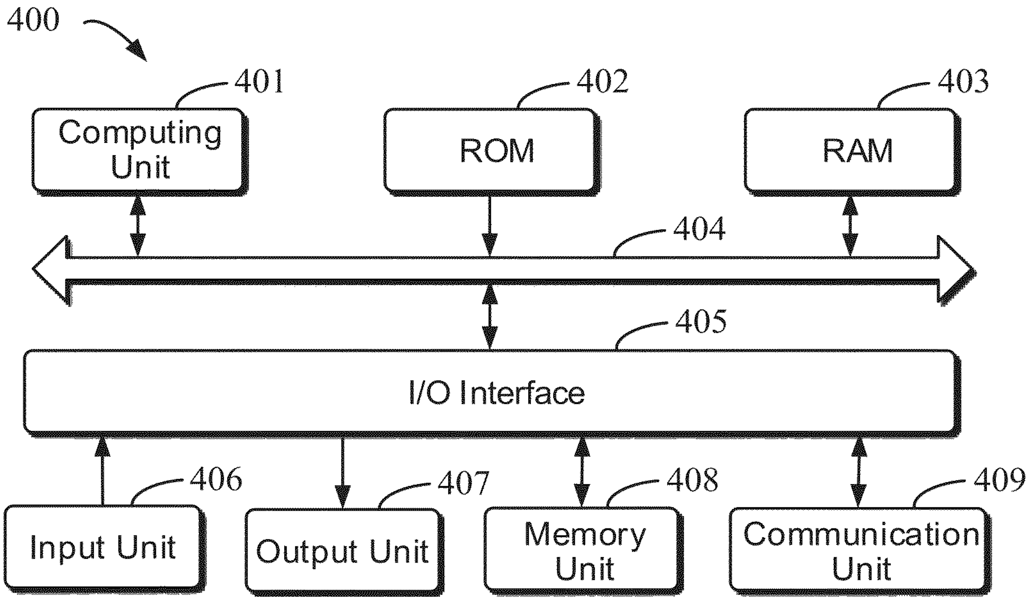
FIG. 4 is a block diagram of an electronic apparatus used for implementing a method for generating a multi-modality image set, in accordance with some embodiments of the present disclosure.

In some embodiments, the electronic apparatus may be the image server shown in FIG. 1 above. FIG. 4 is a block diagram of an electronic apparatus used for implementing a method for generating a multi-modality image set, in accordance with some embodiments of the present disclosure.

The electronic apparatus 400 is intended to represent various forms of digital computers, such as a laptop computer, a desktop computer, a workstation, a personal digital assistant, a server, a blade server, a mainframe computer, and other suitable computers.

The electronic apparatus 400 may also represent various forms of mobile devices, such as a personal digital assistant, a cellular phone, a smart phone, a wearable device, and other similar computing devices.

The components shown herein, their connections and relationships, and their functions are examples only and are not intended to limit implementations of some embodiments of the present disclosure.

As shown in FIG. 4, the electronic apparatus 400 includes a computing unit 401. The computing unit 401 may execute various appropriate actions and processes according to a computer program stored in a read only memory (ROM) 402 or a computer program loaded from a memory unit 408 to a random access memory (RAM) 403.

Various programs and data required for the operation of the electronic apparatus 400 may further be stored in the RAM 403. The calculation unit 401, the ROM 402, and the RAM 403 are connected to each other through a bus 404. An input/output (I/O) interface 405 is further connected to the bus 404.

A plurality of components in the electronic apparatus 400 are connected to the I/O interface 405. The plurality of components includes an input unit 406, such as a keyboard and a mouse; an output unit 407, such as various types of displays and speakers; a memory unit 408, such as a disk and an optical disk; and a communication unit 409, such as a network card, a modem, and a wireless communication transceiver.

The communication unit 409 allows the electronic apparatus 400 to exchange information or data with other devices through a computer network such as the Internet and at least one of various telecommunication networks.

The computing unit 401 may be at least one of various general purpose processing components or special purpose processing components having processing and computing capabilities.

Some examples of computing unit 401 include, but are not limited to, a central processing unit (CPU), a graphics processing unit (GPU), various dedicated artificial intelligence (AI) computing chips, various computing units that run machine learning model algorithms, a digital signal processor (DSP), and any appropriate processor, controller, microcontroller, etc. The computing unit 401 executes the various methods and processes described above, such as the method for generating the multi-modality image set.

For example, in some embodiments, the method for generating the multi-modality image set may be implemented as a computer software program tangibly included in a machine-readable medium, such as in the memory unit 408.

In some embodiments, part or all of the computer program may be loaded onto the electronic apparatus 400 through at least one of the ROM 402 or the communication unit 409.

In some embodiments, part or all of the computer program may be installed onto the electronic apparatus 400 through at least one of the ROM 402 or the communication unit 409.

In some embodiments, part or all of the computer program may be loaded and installed onto the electronic apparatus 400 through at least one of the ROM 402 or the communication unit 409.

In a case where the computer program is loaded into the RAM 403 and executed by the computing unit 401, one or more steps of the method for generating the multi-modality described above may be executed. Alternatively, in some other embodiments, the computing unit 401 may be configured to perform the method for generating the multi-modality in any other appropriate method (e.g., by means of firmware).

Various implementations of the systems and techniques described above in the context may be in one of a digital electronic circuit system, an integrated circuit system, a field programmable gate array (FPGA), an application specific integrated circuit (ASIC), an application specific standard parts (ASSP), a system on a chip (SOC), a complex programmable logic device (CPLD), a computer hardware, a firmware, a software, or a combination thereof.

In some embodiments, these various implementations may include implementations in one or more computer programs.

In some embodiments, the one or more computer programs are executable on a programmable system including at least one programmable processor. In some embodiments, the one or more computer programs may be interpreted on a programmable system including at least one programmable processor. In some embodiments, the one or more computer programs are executable and interpreted on a programmable system including at least one programmable processor.

The programmable processor, which may be a special purpose or general purpose programmable processor, may receive data and instructions from a memory system, at least one input device, and at least one output device, and transmit data and instructions to the memory system, the at least one input device, and the at least one output device.

Program codes for implementing the methods in some embodiments of the present disclosure may be written in any combination of one or more programming languages. Such program codes may be provided to a processor or controller of a general purpose computer, a special purpose computer, or other programmable data processing device such that the program code, when executed by the processor or controller, causes the functions or operations set forth in at least one of the flowcharts or the block diagrams to be performed.

The program codes may be executed entirely on the machine, partially on the machine, partially on the machine as a stand-alone software package and partially on a remote machine, or entirely on a remote machine or server.

In some embodiments of the present disclosure, a machine-readable medium may be a tangible medium that may contain or store a program for use by or in connection with instructions to execute system, device, or apparatus.

The machine-readable medium may be a machine-readable signal medium or a machine-readable storage medium. Machine-readable media may include, but are not limited to, electronic, magnetic, optical, electromagnetic, infrared, or semiconductor systems, apparatuses or devices, or any suitable combination of the foregoing.

For example, the machine-readable storage medium may include an electrical connection based on one or more wires, a portable computer disk, a hard disk, a random-access memory, a read-only memory, an erasable programmable read only memory (EPROM or flash memory), an optical fiber, a convenient compact disc read-only memory (CD-ROM), an optical storage device, a magnetic storage device, or any suitable combination of the foregoing.

To provide interaction with a user, the systems and techniques described herein may be implemented on a computer. The computer has: a display device, such as a cathode ray tube (CRT) or liquid crystal display (LCD) monitor, for displaying information to the user; and a keyboard and a pointing device (e.g., a mouse or trackball) through which the user may provide input to the computer.

Other kinds of devices may also be used to provide interaction with the user. For example, the feedback provided to the user may be any form of sensory feedback (e.g., visual feedback, auditory feedback, or tactile feedback); and may be provided in any form, including acoustic input, speech input, or tactile input) to receive input from the user.

The systems and techniques described herein may be implemented in a computing system including back-end components (e.g., as a data server), or a computing system including middleware components (e.g., an application server), or a computing system including front-end components (e.g., a user's computer having a graphical user interface or web browser through which the user may interact with implementations of the systems and technologies described herein), or a computing system including any combination of such backend components, middleware components, or front-end components.

The components of the system may be interconnected by any form or medium of digital data communication (e.g., a communications network). Examples of communication networks include: local area network (LAN), wide area network (WAN), and the Internet.

Computer systems may include clients and servers. Clients and servers are generally remote from each other and typically interact over a communications network. The relationship of client and server is created by computer programs running on corresponding computers and having a client-server relationship with each other. The server may be a cloud server, or a distributed system server, or a server combined with a blockchain.

It should be understood that various forms of the process shown above may be used, with steps reordered, added or deleted. For example, various steps described in the present disclosure may be executed in parallel, sequentially, or in a different order. As long as the desired results of the technical solution of the present disclosure can be achieved, the present disclosure is no limited thereto.

The above descriptions are merely specific implementation manners of the present disclosure, but the protection scope of the present disclosure is not limited thereto. It will be understood by those skilled in the art that various modifications, combinations, sub-combinations and substitutions may be made depending on design requirements and other factors. Any modifications, equivalent substitutions, improvements, etc. made within the spirit and principles of the present disclosure shall be included in the protection scope of the present disclosure.

What is claimed is:

1. A method for generating a multi-modality image set, comprising:

obtaining a first modality image of a target for radiotherapy; wherein the first modality image is an image generated from the target for radiotherapy, and the target for radiotherapy is injected with a tracer; and performing a first modality conversion on the first modality image to obtain the multi-modality image set of the target for radiotherapy; wherein after the performing the first modality conversion on the first modality image to obtain the multi-modality image set of the target for radiotherapy, the method further comprises:

storing the multi-modality image set of the target for radiotherapy in an image database according to an object identification of the target for radiotherapy; wherein the image database is used to store object identifications of a plurality of targets for radiotherapy and corresponding multi-modality image sets; and performing a second modality conversion on the first modality image of the target for radiotherapy to obtain a second modality image of the target for radiotherapy, in response to the target for radiotherapy in the image database lacking the second modality image in the multi-modality image set.

2. The method according to claim 1, further comprising:

obtaining vital sign data of the target for radiotherapy at a current moment;

wherein the performing the first modality conversion on the first modality image to obtain the multi-modality image set of the target for radiotherapy, includes:

performing the first modality conversion on a first modality image of the target for radiotherapy at a historical moment based on the vital sign data of the target for radiotherapy at the current moment, so as to obtain a multi-modality image set matched with the vital sign data of the target for radiotherapy at the current moment.

3. The method according to claim 2, wherein the obtaining the vital sign data of the target for radiotherapy at the current moment, includes:

performing a contour reconstruction on vital sign data of the target for radiotherapy at a historical moment, so as to obtain the vital sign data of the target for radiotherapy at the current moment.

4. The method according to claim 1, wherein the image database is further used to store object identifications of the plurality of targets for radiotherapy at different moments and corresponding multi-modality image set;

the method further comprises:

in response to lack of a first modality image at a first moment of the target for radiotherapy in the image database, determining timing difference information based on at least one modality image in a multi-modality image set at the first moment and at least one modality image in a multi-modality image set at a second moment; wherein the timing difference information is used to characterize a difference in changes of the target for radiotherapy between the first moment and the second moment; and converting a first modality image at the second moment into the first modality image at the first moment based on the timing difference information, so as to obtain the first modality image of the target for radiotherapy at the first moment.

5. The method according to claim 1, wherein the performing the first modality conversion on the first modality image to obtain the multi-modality image set of the target for radiotherapy, includes:

extracting the tissue structure information of the target for radiotherapy from the first modality image, and performing the first modality conversion on the first modality image based on the tissue structure information, so as to obtain the multi-modality image set of the target for radiotherapy; wherein the tissue structure information is used to characterize a tissue structure of a site to be radiotherapy of the target for radiotherapy.

6. The method according to claim 1, wherein after the performing the first modality conversion on the first modality image to obtain the multi-modality image set of the target for radiotherapy, the method further comprises:

selecting a target modality image that satisfies a preset condition from the multi-modality image set; wherein the target modality image is used to perform at least one of an image registration process, an image fusion process, an image guidance process and a radiotherapy plan generation process of the target for radiotherapy.

7. The method according to claim 1, wherein, in a case where the first modality image is an MRI image, the multi-modality image set includes at least one of the MRI image, a CT image, a CBCT image, a PET image, a PET-MRI image, a PET-CT image, and an optical epidermal image;

in a case where the first modality image is a PET-CT image, the multi-modality image set includes at least one of a CT image, a CBCT image, a PET image, the PET-CT image, and an optical epidermal image.

8. The method according to claim 1, wherein the first modality image is an MRI image generated by an MRI apparatus, and the tracer is a sugar tracer.

9. An electronic apparatus, comprising:

at least one processor; and a memory communicatively connected to the at least one processor; wherein the memory stores instructions executable by the at least one processor, and the instructions are executed by the at least one processor, so as to enable the at least one processor to be configured to:

obtain a first modality image of a target for radiotherapy; wherein the first modality image is an image generated from the target for radiotherapy, and the target for radiotherapy is injected with a tracer; and perform a first modality conversion on the first modality image to obtain the multi-modality image set of the target for radiotherapy;

after performing the first modality conversion on the first modality image to obtain the multi-modality image set of the target for radiotherapy, the electronic apparatus is further configured to:

store the multi-modality image set of the target for radiotherapy in an image database according to an object identification of the target for radiotherapy; wherein the image database is used to store object identifications of a plurality of targets for radiotherapy and corresponding multi-modality image sets; and perform a second modality conversion on the first modality image of the target for radiotherapy to obtain a second modality image of the target radiotherapy, in response to the target for radiotherapy in the image database lacking the second modality image in the multi-modality image set.

10. The electronic apparatus according to claim 9, further configured to: obtain vital sign data of the target for radiotherapy at a current moment;

wherein the electronic apparatus is further configured to:

perform the first modality conversion on a first modality image of the target for radiotherapy at a historical moment based on the vital sign data of the target for radiotherapy at the current moment, so as to obtain a multi-modality image set matched with the vital sign data of the target for radiotherapy at the current moment.

11. The electronic apparatus according to claim 10, further configured to:

perform a contour reconstruction on vital sign data of the target for radiotherapy at a historical moment, so as to obtain the vital sign data of the target for radiotherapy at the current moment.

12. The electronic apparatus according to claim 9, wherein the image database is further used to store object identifications of the plurality of targets for radiotherapy at different moments and corresponding multi-modality image set;

the electronic apparatus is further configured to:

in response to lack of a first modality image at a first moment of the target for radiotherapy in the image database, determine timing difference information based on at least one modality image in a multi-modality image set at the first moment and at least one modality image in a multi-modality image set at a second moment; wherein the timing difference information is used to characterize a difference in changes of the target for radiotherapy between the first moment and the second moment; and convert a first modality image at the second moment into the first modality image at the first moment based on the timing difference information, so as to obtain the first modality image of the target for radiotherapy at the first moment.

13. The electronic apparatus according to claim 9, further configured to:

extract the tissue structure information of the target for radiotherapy from the first modality image, and perform the first modality conversion on the first modality image based on the tissue structure information, so as to obtain the multi-modality image set of the target for radiotherapy; wherein the tissue structure information is used to characterize a tissue structure of a site to be radiotherapy of the target for radiotherapy.

14. The electronic apparatus according to claim 9, wherein after performing the first modality conversion on the first modality image to obtain the multi-modality image set of the target for radiotherapy, the electronic apparatus is further configured to:

select a target modality image that satisfies a preset condition from the multi-modality image set; wherein the target modality image is used to perform at least one of an image registration process, an image fusion process, an image guidance process and a radiotherapy plan generation process of the target for radiotherapy.

15. The electronic apparatus according to claim 9, wherein, in a case where the first modality image is an MRI image, the multi-modality image set includes at least one of the MRI image, a CT image, a CBCT image, a PET image, a PET-MRI image, a PET-CT image, and an optical epidermal image;

in a case where the first modality image is a PET-CT image, the multi-modality image set includes at least one of a CT image, a CBCT image, a PET image, the PET-CT image, and an optical epidermal image.

16. A non-transitory computer-readable storage medium storing computer program instructions that, when executed by a processor, cause the processor to implement the method for generating the multi-modality image set according to claim 1.

* * * * *